(12) United States Patent
Pieringer (10) Patent No.: US 9,833,296 B2
(45) Date of Patent: Dec. 5, 2017

(54) SURGICAL MARKER (75) Inventor: Gary J. Pieringer, Shrewsbury, NJ (US)

(73) Assignee: VISCOT MEDICAL, LLC, East Hanover, NJ (US)

( * ) Notice: Subject to any disclaimer, the term of this patent is extended or adjusted under 35 U.S.C. 154(b) by 1989 days.

(21) Appl. No.: 12/110,970

(22) Filed: Apr. 28, 2008

(65) Prior Publication Data

US 2008/0269694 A1   Oct. 30, 2008

Related U.S. Application Data

(60) Provisional application No. 60/914,350, filed on Apr. 27, 2007.

(51) Int. Cl.
*A61B 90/00* (2016.01)

(52) U.S. Cl.
CPC ........ *A61B 90/39* (2016.02); *A61B 2090/395* (2016.02); *A61B 2090/3916* (2016.02)

(58) Field of Classification Search
CPC ...................................... A61B 90/39
USPC ... 401/170, 171, 176, 179, 182, 187, 188 R, 401/188 A, 198; 604/2
See application file for complete search history.

(56) References Cited

U.S. PATENT DOCUMENTS

| | | | |
|---|---|---|---|
| 3,212,685 A * | 10/1965 | Swan et al. | 401/172 |
| 5,253,942 A * | 10/1993 | Stokes | 401/176 |
| 5,496,304 A | 3/1996 | Chasan | |
| 5,909,978 A | 6/1999 | Giordano et al. | |
| 6,056,737 A | 5/2000 | Rosen | |
| 6,197,034 B1 | 3/2001 | Gvozdic et al. | |
| 6,436,105 B1 | 8/2002 | Passmore | |
| 6,676,322 B1 * | 1/2004 | Leung | 401/205 |
| 6,695,517 B2 | 2/2004 | Witz et al. | |
| 6,986,620 B2 * | 1/2006 | Abbas | 401/188 A |
| 7,581,899 B2 * | 9/2009 | May et al. | 401/133 |
| 2006/0247516 A1 | 11/2006 | Hess et al. | |

* cited by examiner

*Primary Examiner* — Tuan N Nguyen
(74) *Attorney, Agent, or Firm* — Moser Taboada; Alan Taboada (57) ABSTRACT

Embodiments of surgical markers for marking internal and external tissues are provided herein. In some embodiments, a surgical marking device for marking tissue may include a body including an at least partially hollow interior, a first end and a second end; a tip coupled to the body at the second end; and a plunger movably coupled to the body at the first end and configured to control a pressure within the at least partially hollow interior of the body via movement of the plunger relative to the body, wherein the pressure control may control a flow of ink outward of the body via the tip during use. Alternatively, in some embodiments, a squeezable bulb may be provided in place of the plunger, the squeezable bulb having an interior volume fluidly coupled to the body, wherein a pressure within the body may be controlled via the squeezable bulb.

15 Claims, 4 Drawing Sheets

SURGICAL MARKER

CROSS-REFERENCE TO RELATED APPLICATIONS

This application claims the benefit of U.S. Provisional Patent Application entitled "SURGICAL MARKER," having Ser. No. 60/914,350, and filed Apr. 27, 2007, which is hereby incorporated by reference in its entirety.

BACKGROUND OF THE INVENTION

Field of the Invention

Embodiments of the present invention generally relate to apparatus for marking and, more specifically, to apparatus for marking skin and other living tissue during surgical procedures.

Description of the Related Art

During surgical procedures, occasions arise in which it becomes necessary or desirable for the surgeon to apply marks to patient tissue. More particularly, surgeons performing invasive surgery will often mark skin, internal organs, bone, muscle, tendons, or the like. Such marking is often made more difficult by the presence of blood, viscous solids, oils, greases, debris, and the like, on or near the tissue which can contaminate the ink dispensing end of the marking device, thereby partially or completely blocking the flow of ink. While such contaminants may sometimes be cleaned from the ink dispensing end of the writing device, often, the contaminants may cause the dispensing end of the marking device to become clogged. Also, even where cleaning is feasible, additional contamination may often occur soon thereafter.

Accordingly, some marking devices have flexible barrels that facilitate squeezing of the marking device to promote an increased ink flow that compensates for, or overcomes, any contamination present in or on the ink dispensing end of the marking device. However, as such devices require squeezing, this may become tiresome or unwieldy for the operator. This problem may further be exacerbated by long surgeries wherein a surgeon may become progressively more fatigued as the surgery continues.

Thus, there is a need for apparatus for marking tissue in a reliable manner despite the recurring and continuing presence of contaminants.

SUMMARY OF THE INVENTION

Embodiments of surgical markers for marking internal and external tissues are provided herein. In some embodiments, a surgical marking device for marking tissue may include a body including an at least partially hollow interior, a first end and a second end; a tip coupled to the body at the second end; and a plunger movably coupled to the body at the first end and configured to control a pressure within the at least partially hollow interior of the body via movement of the plunger relative to the body, wherein the pressure control may control a flow of ink outward of the body via the tip during use.

In some embodiments, the body and the plunger can include respective opposing reaction surfaces to facilitate the manual generation and application of a compressive force for purposes of moving the plunger deeper into the body. In some embodiments, the body and the plunger can include respective complementary threads for purposes of moving the plunger deeper into the body via a screwing motion.

In some embodiments, a surgical marking device for marking tissue may include a body including an at least partially hollow interior, a first end and a second end; a tip coupled to the body at the second end; and a squeezable bulb having an interior volume fluidly coupled to the body at the first end, wherein a pressure within the body may be controlled via the squeezable bulb, and wherein the pressure control may control a flow of ink outward of the body via the tip during use.

In some embodiments, a surgical marking device for marking tissue may include a body including an at least partially hollow interior, a first end and a second end; a tip coupled to the body at the second end; a pressure control mechanism for controlling a pressure within the body and a flow of ink outward of the body via the tip during use; and a pressure release valve for relieving the pressure within the body.

Other inventive aspects are also included and described herein.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical or similar reference numerals (e.g., having identical digits in the tens and units places) have been used, where possible, to designate identical or functionally similar elements that are common to one or more of the figures.

DETAILED DESCRIPTION

The present invention provides a marker for use in marking a patient during invasive surgery. The marker advantageously provides a controllably pressurizable chamber in which ink is stored to facilitate increased ink flow to compensate for or overcome contaminants that clog or otherwise block flow of ink from a tip of the marker (also sometimes referred to as a nib). The marker further advantageously provides various embodiments of pressure control mechanisms for creating and/or maintaining a desired flow of ink during use. The pressure control mechanisms may further reduce the effort required to create and/or maintain the desired flow of ink during use, thereby facilitating ease of use, particularly when a surgeon may be fatigued during a lengthy procedure.

Figure 1:
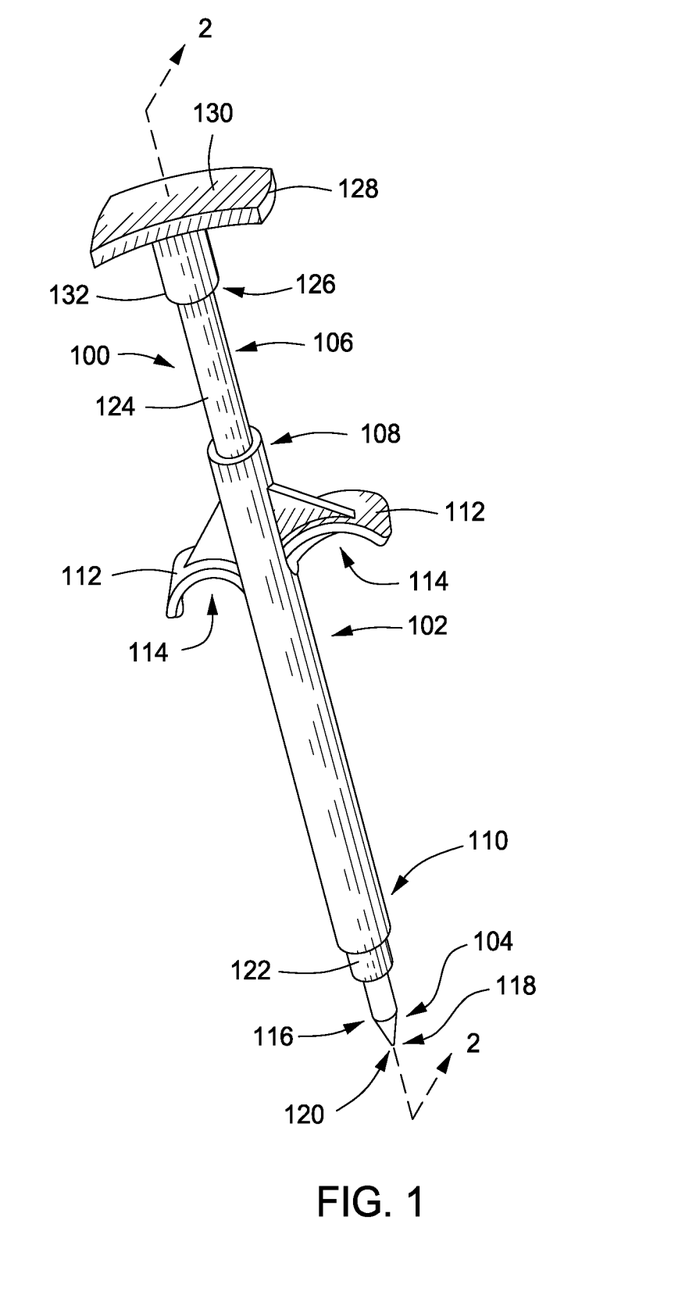
FIG. 1 depicts a perspective view of a marker for marking tissue in accordance with some embodiments of the invention.

FIG. 1 depicts a perspective view of a marker 100 in accordance with some embodiments of the invention. The marker 100 generally includes a body 102, a tip 104, and an actuator, such as a plunger 106. The body 102 is at least partially hollow, and is chargeable with and/or contains ink. The body 102 may be elongate in shape, having an upper end 108 associated with the plunger 106, and a lower end 110 located longitudinally opposite the upper end 108 and associated with the tip 104.

In some embodiments, the body 102 is not necessarily elongated in shape, and/or the plunger 106 and the tip 104 of the marker 100 may be associated with the same end of the body 102, and/or with separate but not necessarily longitudinally opposite regions of the body. In some embodiments, the body 102 is of a substantially unitary construction. Alternatively, the body 102 can be an assembly of two or more body parts or components. Part or all of the body 102 can be formed via an injection molding process. In some embodiments, such as that depicted in FIG. 1, the body 102 includes flanges 112 at or near where the plunger 106 is coupled to the body 102 to facilitate ease of operation of the plunger 106. For example, in the embodiment of FIG. 1, the flanges 112 are disposed at or near the upper end 108 of the body, and the flanges 112 define horizontally oriented reaction surfaces 114 against which a user may press his or her fingers for applying upward force to the body 102 and/or downward force to the plunger 106 during use of the marker 100. In some embodiments, the body 102 may contains other reaction surfaces, such as vertically-oriented reaction surfaces (see, for example, those described below with respect to FIG. 3), and/or radially or axially curved reaction surfaces. In embodiments in which reaction surfaces are provided on the body 102, such reaction surfaces may be knurled and/or otherwise roughened to facilitate stable and reliable operation.

The tip 104 is coupled to the body 102 at the lower end 110 thereof so as to facilitate the outward flow of ink during use. The tip 104 may be coupled to the body by any suitable means, such as gluing, bonding, press-fit, or the like. In some embodiments, the tip 104 may be coupled directly to the body 102. Alternatively, the tip 104 may be indirectly coupled to the body 102 via a collet (not shown in FIG. 1), and/or via an intermediate part or component, such as via an ink cartridge (not shown in FIG. 1) to which the tip 104 is attached, and/or into which an upper portion of the tip 104 at least partially extends, and from which the tip 104 draws ink (see, for example, the embodiment shown and described hereinbelow with reference to FIG. 2). Such ink cartridge (not shown in FIG. 1) can be substantially entirely disposed within the body 102, substantially entirely disposed outside of the body 102, or partially disposed within, and partially disposed outside of, the body 102. In some embodiments, the tip 104 extends at least partially into the body 102, and/or at least partially into a corresponding ink cartridge (not shown in FIG. 1) contained entirely within the body 102.

In at least some embodiments, the tip 104 is a fluid transfer element, or nib, fluidly coupled to the body 102 so as to permit and/or promote flow of ink from the body 102 into the tip 104 (for example, by capillary action through the nib). For example, the tip 104 can be coupled to the body 102 in such a way as to render the tip 104 sensitive to changes in a gas pressure within the body 102, e.g., such that incremental increases in such gas pressure will tend to increase a capillary pressure of liquid ink contained within the tip 104. In some embodiments, the tip 104 is a porous assembly of fibers or fibrous flow-inducing channels, such as fibers or channels composed of, for example, felt, and/or of a synthetic or natural material (e.g., Nylon®, polyester, and/or other plastic or resin), and oriented substantially vertically, and/or randomly laterally or axially distributed within a volume of the tip 104. Further, in some embodiments, such as that depicted in FIG. 1, the tip 104 has a shape that includes a section 116 of a relatively larger cross-sectional width or thickness at or near where the tip 104 is coupled to the body 102, and a section 118 below the section 116 along which the tip 104 tapers down from the larger dimension to form a relatively smaller marking point 120 suitable for forming lines of ink on tissue. Some such embodiments include conical, parabolic, and/or wedge-shaped tips 104. Many other possible shapes for the tip 104 are contemplated, including examples characterized by a relatively constant cross-sectional width, diameter, and/or or thickness along the length of the tip 104, such that the tip 104 does not necessarily taper down to form a relatively finer marking point. The marking point 120 of the tip 104 may be shaped and/or dimensioned so as to permit formation of ink lines of relatively large widths, relatively fine widths, and/or intermediate widths.

In some embodiments, the tip 104 may be coupled to the lower end 110 of the body 102 in a manner that facilitates pressurization of gas contained within the body 102 by, for example, at least partially sealing the body 102 against and/or restricting leakage of such gas outward of the lower end 110. The body 102 may include a crimp 122 at and along the lower end 110 for purposes of sealing against gas leakage therethrough. Alternatively, the tip 104 may be press fit, sonically welded, or otherwise coupled to the lower end 110 of the body 102 in a manner that facilitates controlled pressurization of the marker 100 during use. The tip 104 may or may not have an air channel, or vent (not shown), for allowing air within the body to leak out. Conventional tips for markers typically have a tip vent. However, in some embodiments of the present invention, the tip 104 does not have a vent (or has a sealed vent). When the tip vent is sealed or otherwise not present, retraction of the plunger may be utilized to stop the flow of ink (e.g., by reducing the internal pressure of the marker, within the body). Embodiments of the present invention without a tip vent also minimizes "ink blow by" (excessive ink spraying out if the plunger is pressed too forcefully).

In some embodiments, including that shown in FIG. 1, the body 102 is chargeable with, and/or contains, ink in a liquid form, such as gentian violet. In some embodiments, the ink provided in the marker may be an ink approved by the Food and Drug Administration (FDA) for use in internal and/or external marking procedures. In some embodiments, the body 102 includes or is adapted to receive or be coupled to an ink cartridge (not shown in FIG. 1) that contains such ink and that can be removed and replaced when the ink contained therein is spent. In some embodiments, the tip 104 may be preassembled together with the ink cartridge. In some embodiments, the tip 104 is adapted to be readily decoupled from the ink cartridge and retained for re-use in conjunction with a new ink cartridge after the spent ink cartridge has been removed from the body 102. The tip 104 may be affixed (e.g., more or less permanently) to the body 102 in such a way as to permit the tip to readily achieve a fluid coupling with a replacement ink cartridge (not shown) as the same is installed on or in the body 102. In some embodiments, the body 102 is chargeable with ink for purposes of liquid communication with a permanent or replaceable tip 104 without necessarily employing a separate cartridge to contain and/or retain such ink. Additionally, and/or alternatively, in some embodiments, the tip 104 may be configured to be selectively readily removed from the body 102 and replaced with a new tip 104 of a similar or a different shape, and/or that is associated with the same, or with a different, ink line width.

The plunger 106 is movably coupled to the body 102, for example, to permit the plunger 106 to move relative thereto so as to increase a gas pressure within the body 102 and thereby increase, as needed, and/or as desired, a flow of ink outward of the body 102 via the tip 104. The plunger 106 may generally be movable toward and/or away from the body 102 so as to effect a controlled pressurization or depressurization of the body 102. The marker 100 may thus be controllably pressurized or depressurized, as needed, or as desired (e.g., to increase ink flow during use or to decrease and/or stop ink flow as desired). In some embodiments, the plunger 106 may have a limited range of motion to prevent the plunger 106 from separating the tip 104 from the body 102. For example, a stop 132 may be disposed on one or more of the body 102 or the plunger 106 (or any other suitable location) to restrict the downward motion of the plunger 106 sufficiently to prevent the plunger 106 from separating the tip 104 from the body 102. In another example, the plunger 106 may have a length such that the maximum travel of the plunger 106 will not cause interference with the tip 104 in a manner as described above.

In some embodiments, the plunger 106 may be selectably reciprocally movable relative to the body 102, e.g., for purposes of controlled pressurization and depressurization of the body 102. In some embodiments, the plunger 106 is both reciprocally movable relative to the body 102, and biased so as to tend to retract in a direction opposite that which is associated with a pressurization stroke of the plunger 106 relative to the body 102. In accordance with some embodiments, a user is permitted to urge or move the plunger 106 in a direction associated with a pressurization stroke of the plunger 106 (e.g., either toward and/or inward of the body 102, or away from and/or outward of the body 102) to an extent of a predefined distance or 'throw' of the plunger 106, so as to compress and/or reduce a volume of a quantity of air contained in a chamber (not shown in FIG. 1) of the body 102 to a predefined extent or amount, after which the plunger 106 is allowed to retract in the opposite direction (e.g., either away from and/or outward of the body 102, or inward and/or toward therefrom, as the case may be) to a default position relative to the body 102. Once having reached such default position, the plunger 106 is prepositioned for another such cycle of compression and/or volume reduction. In some embodiments, the marker 100 may include one or more resilient members (not shown), such as a coil spring, a leaf spring, an elastic band, or the like, or another type of return mechanism, such as a pressurizable chamber/piston combination or the like, disposed within or attached to the body 102, for purposes of retracting the plunger 106 after it has reached the end of its throw. With respect to such embodiments, each additional such cycle (e.g., including a user-caused movement followed by an automatic retraction of the plunger 106 relative to the body 102) is adapted to incrementally increase a gas pressure within the body 102 as compared to that achieved by the previous such cycle. The user is thereafter permitted to execute such additional cycles as may be necessary to bring about the desired result, e.g., sufficient ink flow through the tip 104.

In some embodiments, the plunger 106 may include an arm 124 that extends toward and through the upper end 108 of the body 102 and, to at least some extent, into the hollow interior (not separately shown) of the body 102. A seal (not separately shown in FIG. 1) is generally formed within the body between the arm 124 of the plunger 106 and the hollow interior of the body 102 that facilitates pressurization of gas contained within the body 102 by at least partially sealing the body 102 against leakage of such gas outward of the upper end 108. In some embodiments, no such seal is included between the arm 124 of the plunger 106 and the body 102. For example, the arm 124 of the plunger 106 may be adapted to press against, deform, and/or otherwise compress or reduce a volume of a pressurizable chamber (not shown in FIG. 1) formed by and/or within the body 102.

In some embodiments, such as that depicted in FIG. 1, the plunger 106 further includes an upper end 126 and a flange 128 located at the upper end 126, the flange 128 defining a horizontally oriented reaction surface 130 against which a user may press his or her thumb for applying downward force to the plunger 106 during use of the marker 100. In some other embodiments, the plunger 102 contains differently oriented reaction surfaces, such as vertically-oriented reaction surfaces (see, for example, those shown and described hereinbelow with respect to FIG. 3), and/or radially or axially curved reaction surfaces. In some embodiments, the reaction surfaces may be knurled and/or otherwise roughened, so as to facilitate stable and reliable urging, grasping and/or turning of the plunger 106.

In some embodiments, the body 102 and/or the plunger 106 may be adapted to allow relatively smooth and/or continuous movement of the plunger 106 relative to the body 102 for purposes of pressurizing the body 102. For example, the plunger 106 and/or the body 102 can include relatively physically smooth surfaces (not separately shown) where the plunger 106 and the body 102 interact, and/or along which a pressure-tight seal (not shown in FIG. 1) is formed therebetween. In some other embodiments thereof, the body 102 and/or the plunger 106 may be adapted to allow incremental and/or relatively discontinuous or stepwise movement of the plunger 106 relative to the body 102 for purposes of pressurizing the body 102, e.g., according to a predefined distance increment. For example, the plunger 106 and/or the body 102 can include one or more physical indentations or elevated features (not separately shown), such as transverse radial or axial detents or ridges, in respective surfaces (not separately shown) where the plunger 106 and the body 102 interact, and/or along which a pressure tight seal (not shown in FIG. 1) is formed therebetween. In the event multiple such indentations and/or detents are provided, the same can be sufficiently closely longitudinally or axially spaced so as to provide a suitably fine degree of control over the position of the plunger 106 relative to the body 102 at any given time.

As noted hereinabove, during use of the marker 100 to mark tissue, viscous solids, oils, greases and/or other debris may collect on the tip 104, potentially reducing the capacity of the tip 104 to dispense the ink contained in the body 102. The plunger 106 can be used to increase a gas pressure within the body 102, thereby developing greater capillary pressure with respect to the hydraulic coupling between the body 102 and the tip 104 and increasing a volume flow of ink from within the body 102 toward and into the tip 104. Such additional ink flow toward and into the tip 104 will in turn tend to force its way out of the tip 104 by, for example, dislodging the contamination present therein, or by finding alternative and/or relatively unblocked paths therethrough, so as to facilitate the marking of tissue despite the ongoing presence of contamination on or within the tip 104.

To use the plunger 106 to increase a gas pressure within the body 102, the user moves the plunger 106 relative to the body 102, thereby compressing the air contained in the body 102, and increasing the gas pressure associated therewith. The increased gas pressure within the body 102 will then impinge with greater force on the quantity of ink disposed therein, thereby increasing the ink flow through the tip 104.

The above-described apparatus and method provides numerous advantages relative to existing apparatus, systems, and methods. For example, to the extent surgeons are unwilling or simply unable to interrupt the flow of a surgical procedure to contend with a problem with ink flow through a surgical marker, the marker 100 will be of great assistance, at least insofar as the marker 100 can significantly alleviate the flow-stanching impact of persistent nib contamination. If the surgeon finds that ink flow through the tip 104 has slowed or stopped, it is not strictly necessary for him or her to interrupt the surgical procedure, e.g., so as to clean the tip 104 or to obtain a new marker. Rather, he or she can simply move the plunger 106 relative to the body 102 as described hereinabove and, in most circumstances, the flow of ink to and/or through the tip 104 will be restored. Even in circumstances in which some cleaning of the tip 104 is necessary, the process of cleaning the tip 104 can be significantly shortened and/or undertaken less frequently based on the ability of the marker 100 to adequately function in the face of persistent nib contamination.

With respect to the particular embodiment shown and described hereinabove with reference to FIG. 1, it is further noted that the reaction surfaces 114, 130 may be conveniently shaped, sized and positioned relative to each other such that the surgeon will be able to execute the above-described movement of the plunger 106 deeper into the body 102 comfortably and easily, e.g., via the manual compressive motion associated with a conventional needle-type syringe. Such a motion is, of course, familiar to the surgeon, and is comfortable at least insofar as it tends to employ the relatively larger and stronger muscles of the hand, thereby facilitating ease of use even after many hours of difficult and tiring surgery, whereby the surgeon's hands and/or fingers may be fatigued. After having pressurized the body 102, the surgeon can proceed to write with the marker 100, using, for example, a grip and a writing pressure similar to those associated with a conventional ink pen or marker.

Figures 2, 2A:
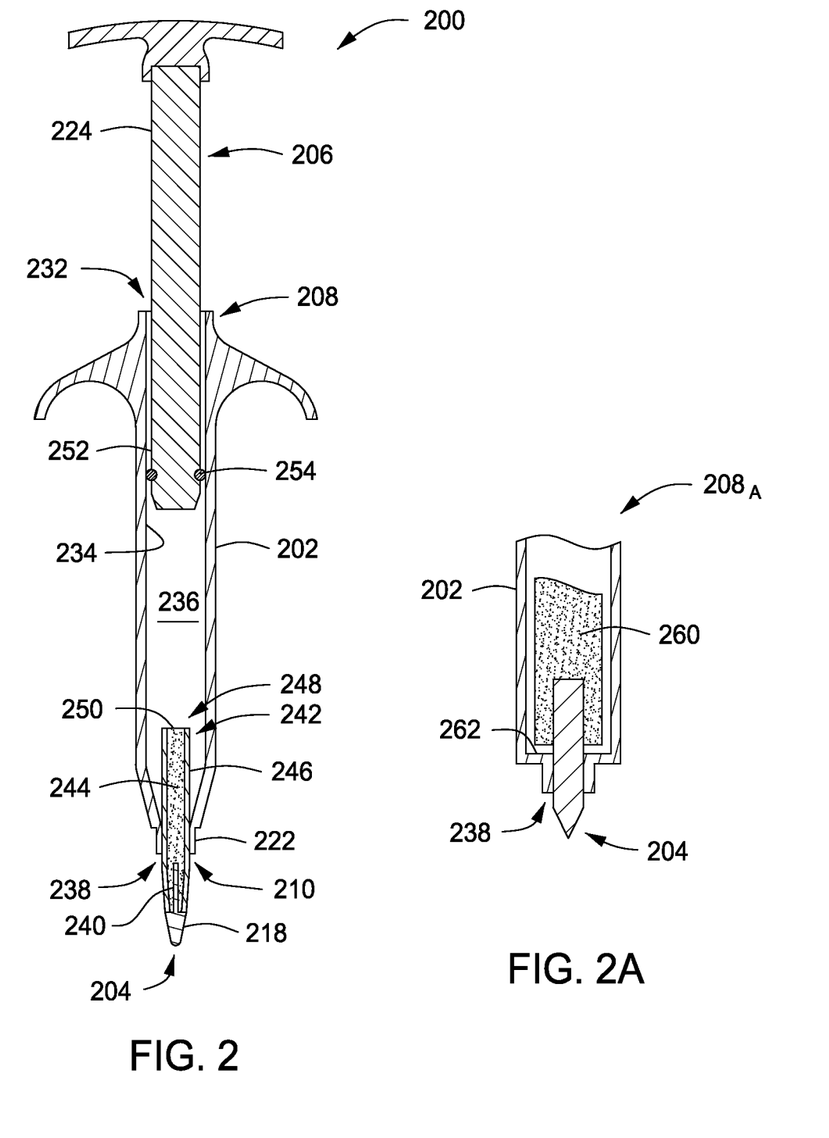
FIGS. 2 and 2A are a cross-sectional side views of a marker marking tissue in accordance with some embodiments of the invention.
Figure 3:
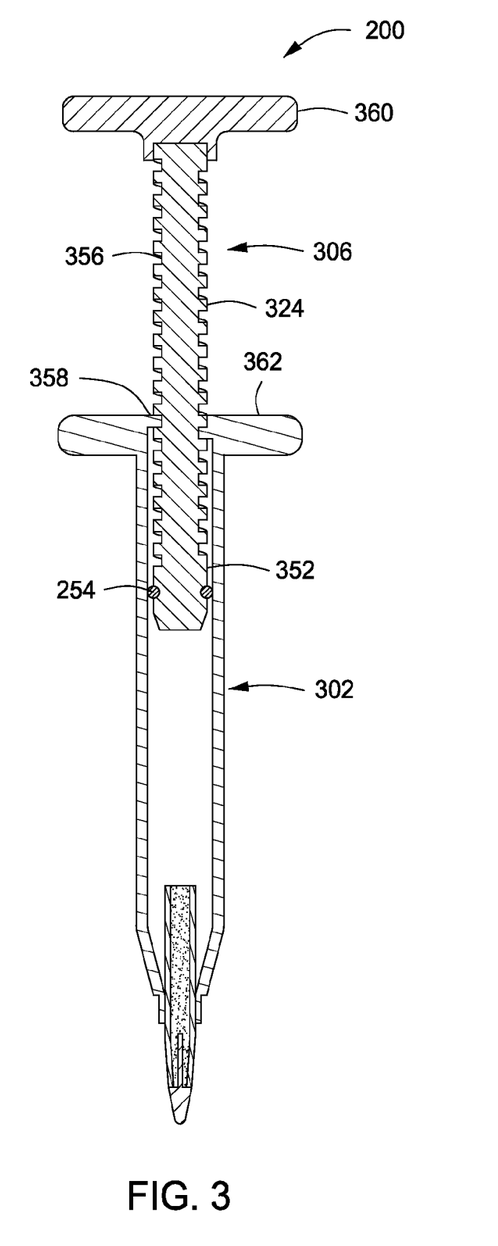
FIG. 3 is a cross-sectional side view of a marker for marking tissue in accordance with some embodiments of the invention.

With respect to the exemplary marker 100 described hereinabove with reference to FIG. 1, and with respect to the method of operation described hereinabove, numerous variations and/or modifications thereof, are also contemplated. For example, FIG. 2 illustrates a variation of the marker 100 shown in FIG. 1, and FIG. 3 illustrates a modified version of the marker 100 shown in FIG. 1. Elements illustrated in FIGS. 2 and/or 3, which correspond, either identically or substantially, to the elements described above with respect to the embodiment of FIG. 1, have been designated by corresponding reference numerals bearing consistently similar digits in the tens and units places. Unless otherwise stated, each of the variations of FIG. 2 and FIG. 3 has a construction and an operation that is substantially structurally and/or functionally similar to that of the embodiment of FIG. 1.

FIG. 2 is a cross-sectional side view of a marker 200 taken along a section line corresponding to section line 2-2 appearing in FIG. 1, the marker 200 being a variation of the marker 100 shown and described hereinabove with reference to FIG. 1. The body 202 includes an opening 232 formed in the upper end 208 of the body 202. The body 202 further includes an interior surface 234 that extends upward to and terminates at the opening 232 formed in the upper end 208, extends downward therefrom toward the lower end 210, and at least partially defines a chamber 236 within the body 202. The body 202 further includes an opening 238 formed in the lower end 210 of the body 202.

The marker 200 may further include an ink cartridge 242 having a buffer 244 that is porous and is capable of retaining ink, and an elongate sleeve 246 that surrounds the buffer 244, and within which the buffer 244 is contained. The tip 204 may include an extension 240 that extends into the buffer 244. Supported and reinforced by the sleeve 246, the buffer 244 engages the extension 240 of the tip 204 in an interference fit within the buffer 244. The buffer 244 and the extension 240 of the tip 204 are in sufficiently close and/or intimate physical contact to enable fluid coupling between the buffer 244 and the tip 204 for purposes of promoting a free flow of ink from the former to the latter. The sleeve 246 includes an axial end 248 that is open, and at which a corresponding axial end 250 of the buffer 244 is exposed to the prevailing gas pressure within the chamber 236. The body 202 accommodates the ink cartridge 242 at the opening 238 formed at the lower end 210 of the body 202. In some embodiments, the body 202 engages the sleeve 246 at the opening 238 in a relatively airtight interference or pressure fit. In some embodiments, the body 202 further includes a crimp 222 formed at the lower end 210 to ensure a tight fit with the sleeve 246. In some embodiments, the body 202 includes an interior lip or collar (not separately shown) at or near the opening 238 to retain the ink cartridge 242 and/or positively prevent the ink cartridge 242 from being urged downward through the opening 238 and/or entirely ejected from the body 202 (e.g., by action of the plunger 206).

It is contemplated that the ink may be retained and or dispensed in the marker in a variety of embodiments in accordance with the teachings contained herein. For example, FIG. 2A depicts a cross sectional view of the marker $200_A$ having a nib or tip 204 press fit into the opening 238 at a lower end of the body 202 of the marker $200_A$. The tip 204 extends into an ink reservoir 260, which may be similar to the buffer 244 described with respect to FIG. 2. A bottom surface 262 of the body 202 provides a bottom support for the ink reservoir 260 and prevents the plunger (not shown) from pushing the ink reservoir 260 too far downwards, which may otherwise result in pushing the tip 204 out of the opening 238. It is contemplated that the tip configuration shown in FIG. 2A may be additionally be utilized in other embodiments, such as those described herein.

The arm 224 of the plunger 206 may include a peripheral surface 252 having a sealing element 254 (for example, a gasket), for example, lodged in an annular groove formed in the peripheral surface 252. The sealing element 254 provides a substantially airtight seal between the interior surface 234 of the body 202 and the peripheral surface 252 of the arm 224. At least in part by virtue of the presence and respective sealing functions of the sealing element 254 disposed between the arm 224 and the body 202, and the crimp 222 formed in the lower end 210 of the body 202 around the sleeve 246 of the ink cartridge 242, the chamber 236 is susceptible to pressurization by action of the plunger 206. The total quantity by weight of the air, or of the air and vapor mixture, contained in the chamber 236 tends not to decrease to any significant extent as the arm 224 advances downward into the chamber 236. This is so not only because of the characteristic compressibility of gases generally (e.g., as compared to liquids (e.g., inks)), but also at least in part due to the respective sealing effects of the crimp 222 and the sealing element 254 described immediately hereinabove. Ink in the ink cartridge 242 and/or in the tip 204 may also tend to seal the chamber 236 to at least some extent against undue and/or abrupt leaks of air or of air and vapor mixtures.

With reference to FIG. 3, the marker 300 includes modifications to the body 102 and to the plunger 106 (see FIG. 1) to facilitate the use of a screwing motion to move the plunger 306 relative to the body 302. More particularly, the arm 324 of the plunger 306 includes a channel 356 formed in the peripheral surface 352 of the arm 324, and the body 302 includes a corresponding inwardly projecting thread 358. The flange 128 of the plunger 106 of the marker 100 of FIG. 1 may be replaced with a transverse arm 360, e.g., functionally similar to corresponding structure of a wingnut. The body 302 may optionally be further equipped with structure of similar functionality in an arm 362. In operation, a user twists the plunger 306 with respect to the body 302 as necessary or as desired, e.g., to move the arm 324 deeper into the body 302. As shown in FIG. 3, each of the channel 356 and the thread 358 is substantially helical in shape, and has straight side walls, such that the arm 324 and the body 302 will tend to rotate smoothly relative to each other without undue risk of binding therebetween. Accordingly, a convenient alternative means of applying compressive force to the air or air and vapor mixture in the pressure chamber 316 is provided that allows fine control without the need for a surgeon to use small hand muscles depleted of strength due to overuse during long surgical procedures.

Other variations and modifications of the embodiments shown and described with reference to FIGS. 1-3 are also possible. For example, the interior and exterior surfaces of the marker 100 may have any cross-sectional shape, such as circular, non-circular curved shapes, straight-sided polygonal shapes, and irregular shapes. The geometry, configuration, and/or placement of the ink cartridge 242 can be modified consistent with exposing ink contained within the buffer 244 to the prevailing gas pressure within the chamber 236. The crimp 222 can be removed and replaced with any other suitable conventional means of affixing the ink cartridge 242 to the body 202, and sealing the interface therebetween, e.g., with a flexible cement, a compressible seal or collar, and/or an ultrasonic weld. The ink cartridge may also be disposed within the body without being attached thereto.

Further, other variations and modifications of mechanisms for depressing the plunger 106, 206, 306 with reference to FIGS. 1-2 are contemplated. For example, such mechanisms can include a ratcheting mechanism whereby a trigger, disposed exterior to the body 102, 202, 302 and operated by the user, may be utilized to incrementally advance the plunger 106, 206, 306 with each depression of the trigger device. The ratcheting mechanism may function via the interface of the trigger with incrementally spaced notches formed in the arm of the plunger, wherein the trigger interfaces with (or causes some other member of the ratcheting mechanism to interface with) the notches to advance the plunger.

Still further variations and modifications are possible. In some embodiments, the marker 100, 200 may be assembled together with, and/or at a marking end of, a longitudinally extended element, (for example, to form an extended length marker. In some embodiments, the plunger 106, 206 itself can of an extended length relative to that of the body 102, 202, (e.g., the plunger or actuation mechanism may be remote from the body) and/or can be laterally flexible (e.g., incorporating a wire-in-sleeve cable assembly to facilitate remote manual foot-actuated operation by the surgeon, or by an assisting nurse or other third party).

Figure 4:
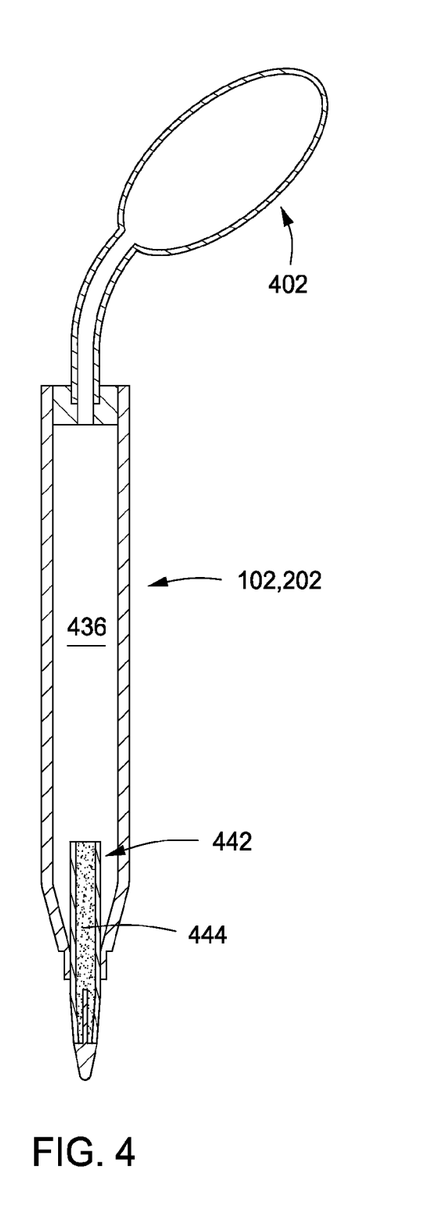
FIG. 4 is a cross-sectional side view of a marker for marking tissue in accordance with some embodiments of the invention.

In some embodiments, for example, as depicted in FIG. 4, the plunger 106 of the marker 100 of FIG. 1, and/or the plunger 206 of the marker 200 of FIG. 2, can be omitted and replaced with a squeezable bulb 402, bottle, or the like, coupled to the respective bodies 102, 202. Such a bulb can be kept in fluid communication with a chamber 436 (similar to the chamber 236), and in at least some embodiments, can contain a volume of liquid ink. In embodiments, such a bulb can be remotely disposed with respect to the chamber 436 (e.g., so as to permit remote manual or foot-operated squeezing or other actuation). In other embodiments, such a bulb can partially or fully embody the chamber 436 itself, e.g., surrounding an ink cartridge 442 and/or the ink buffer 444 (similar to the ink cartridge 242 and the ink buffer 244). In some embodiments, the bulb 402 may also operate as a pump (and optionally a valve), such as is used to inflate (and optionally deflate) a blood pressure monitoring cuff. In some embodiments, the body may be pressurized by means of a electro-mechanical or hydraulic pump, which may be activated by a switch.

In some embodiments, for example, as depicted in FIGS. 5A-D, a pressure release valve may be provided to reduce the pressure within at least the partially hollow interior of the body and/or to prevent the pressure within the body from exceeding a determined amount. The pressure release valve may be disposed in any suitable location, such as, for example, in the wall of the body, in the plunger, as part of the sealing element between the plunger and the hollow interior of the body (e.g., chamber 236, 436), in or proximate the squeezable bulb, or in any portions of the surgical marking device or coupled to the surgical marking device suitable for reducing and/or controlling the pressure within at least the partially hollow interior of the body. The pressure release valve may provide a seal at or below a fixed pressure, above which the valve is designed to leak, or vent, until the pressure is reduced to the fixed pressure at which the valve again provides a seal. In some embodiments, the pressure release valve may provide such a seal at a selectable, or variable pressure that us able to be set by the user as desired.

Figure 5A:
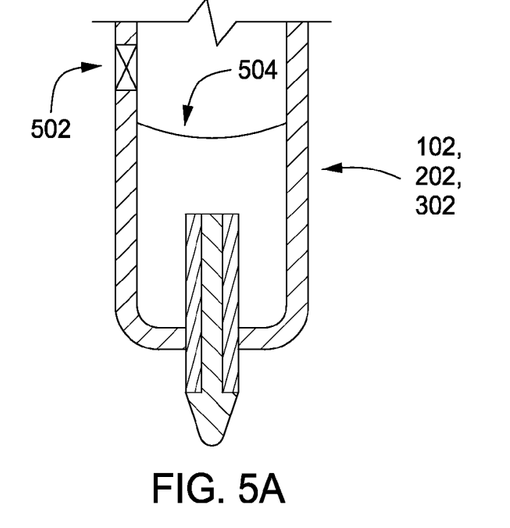
FIGS. 5A-D respectively depict cross-sectional side views of markers for marking tissue in accordance with some embodiments of the invention.

The pressure release valve may be any suitable valve or mechanism, such as for example, a rubber seal or gasket having a small hole for facilitating fluid leakage above a certain pressure, the seal (e.g., 254) disposed between the plunger and the body, a one way valve, or any other suitable pressure release valve or mechanism. For example, as depicted in FIG. 5A, a pressure release valve 502 may be disposed in the wall of the body, thereby facilitating the release of pressure from the hollow interior of the body 102, 202, 302. In some embodiments, as depicted in FIG. 5A, the pressure release valve 502 may be disposed above a maximum ink level 504 of ink contained with the hollow interior. Such a configuration may be appropriate for the purposes of preventing the flow of ink out of the pressure release valve 502 when pressure is applied to the hollow interior via any of the embodiments described above in FIGS. 1-4. In some embodiments, where ink is contained in a cartridge, or otherwise constrained within the body, the pressure release valve 502 may be disposed in other suitable locations in the body.

Figure 5B:
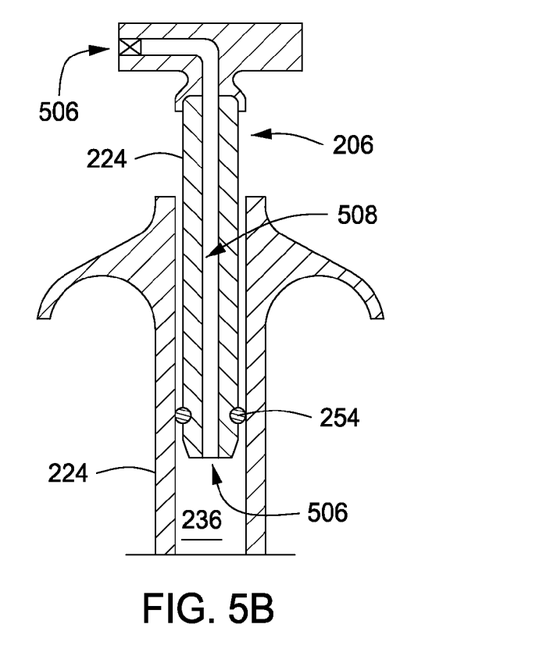

In some embodiments, the pressure release valve may be disposed in either the plunger, the sealing element, or a combination thereof. In some embodiments, and as depicted in FIG. 5B, the pressure release valve 506 may be disposed in the plunger 206. The pressure release valve 506 may be disposed at either end of a passage 508 formed in the plunger 206, allowing for a reduction in pressure in the hollow interior (i.e., chamber 236) of the body 206. The passage 508 may run, for example, longitudinally through the arm 224, terminating at an end of a flange (similar to flange 128) of the plunger 206 or other suitable location (for example, to avoid interference from the hand of the user). The release valve 506 may be disposed at the end of the flange of the plunger 206 as depicted in FIG. 5B. Alternatively, the release valve 506 may be disposed in the longitudinal portion of the plunger, proximate and below the flange, such that the hollow interior 508 would terminate just below the flange (not shown). Further, the above embodiments of the release valve 506 and the passageway 508 can be utilized with the embodiments of the plunger 306 depicted in FIG. 3.

Alternatively or in combination, and as depicted in FIG. 5B, the release valve may be part of the sealing element 254. The sealing element 254 may be suitable for maintaining a seal between the plunger 206 and the body 202 up to a desired pressure, above which the sealing element may leak sufficiently to reduce the pressure with the chamber 236 to a level at or below the desired pressure. The sealing element described above may be utilized with the embodiments of the plunger 306 as described in FIG. 3. Although disclosed in conjunction with a release valve formed as part of the plunger in FIG. 5B, the pressure release valve may be formed in either location alone, or in combination.

Figures 5C, 5D:
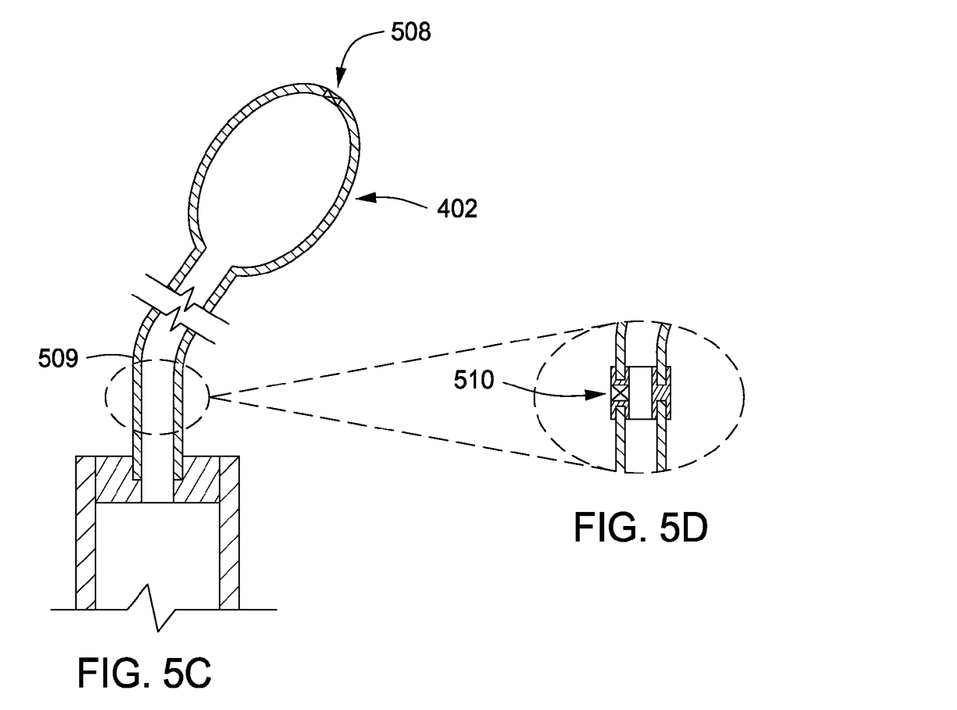

In some embodiments, such as those depicted in FIG. 5C and further applying to the embodiments described in FIG. 4, a pressure release valve 508 may be disposed in the squeezable bulb 402, or alternatively (as shown in FIG. 5D), a pressure release valve 510 may be disposed in the conduit 509 (e.g., flexible tubing) which couples the squeezable bulb 402 to the body. Similar to the embodiments described above, depression of the squeezable bulb 402 may be suitable for creating a desired pressure with the hollow interior of the body. Exceeding the desired pressure may cause the release valve to open, hence reducing the pressure within the hollow interior of the body to a level at or below the desired pressure.

Thus, apparatus and methods for marking tissue in the presence of significant amounts of persistent nib contamination have been provided that advantageously improve over conventional processes and equipment. The features shown in the various embodiments described above may be combined and/or modified by one of ordinary skill in the art without departing from the spirit and scope of the present invention.

While the foregoing is directed to embodiments of the present invention, other and further embodiments of the invention may be devised without departing from the basic scope thereof.

What is claimed is:

1. A surgical marking device for marking tissue, comprising:
   a body including an at least partially hollow interior, a first end, and a second end having an opening;
   an ink disposed within in the at least partially hollow interior of the body, wherein the ink is Food and Drug Administration (FDA) approved for use in internal and/or external marking tissue of a mammal during surgical procedures;
   a tip retained within the opening of the body at the second end, the tip comprising a porous assembly of fibers or fibrous flow-inducing channels fluidly coupled to the body to permit flow of the ink from the body to the tip by capillary action;
   a plunger movably coupled to the body at the first end and configured to control a gas pressure within the at least partially hollow interior of the body via movement of the plunger relative to the body, wherein an increase in the gas pressure increases a pressure of liquid ink contained within the tip and the pressure controls a flow of the ink outward of the body via the tip during use, and wherein the tip is non-reactive with the ink; and
   a pressure release valve for reducing the pressure within the at least partially hollow interior of the body.

2. The device of claim 1, further comprising:
   an ink cartridge at least partially contained within the body and in fluid communication with the tip, the ink cartridge having the ink disposed therein.

3. The device of claim 2, wherein the tip is detachable from a spent ink cartridge and attachable to a replacement ink cartridge that is insertable into the body.

4. The device of claim 1, further comprising:
   opposing reaction surfaces respectively disposed on the body and the plunger to facilitate the manual generation and application of a force for purposes of moving the plunger deeper into the body.

5. The device of claim 1, further comprising:
   complementary threads respectively disposed in the body and the plunger that facilitate control of the position of the plunger with respect to the body via a screwing motion.

6. The device of claim 1, wherein the pressure release valve comprises:
   a gasket disposed between the plunger and the body and suitable for maintaining a seal therebetween up to a desired pressure, and above which the gasket may leak sufficiently to reduce the pressure within the body to a level at or below the desired pressure.

7. The device of claim 1, further comprising:
   a stop coupled to the body and configured to restrict the downward motion of the plunger sufficiently to prevent the plunger from separating the tip from the body.

8. The device of claim 1, wherein the pressure release valve is disposed in the body.

9. A surgical marking device for marking tissue comprising:
   a body including an at least partially hollow interior, a first end, and a second end having an opening;
   an ink disposed within in the at least partially hollow interior of the body, wherein the ink is Food and Drug Administration (FDA) approved for use in internal and/or external marking tissue of a mammal during surgical procedures;
   a tip retained within the opening of the body at the second end, the tip comprising a porous assembly of fibers or fibrous flow-inducing channels fluidly coupled to the body to permit flow of the ink from the body to the tip by capillary action, wherein the tip is non-reactive with the ink;
   a gas pressure control mechanism for controlling a gas pressure within the body, wherein an increase in the gas pressure increases a pressure of liquid ink contained within the tip, and a flow of ink outward of the body via the tip during use; and
   a pressure release valve for relieving the pressure within the body.

10. The device of claim 9, wherein the pressure release valve is disposed in the body.

11. The device of claim 9, wherein the pressure control mechanism comprises a plunger.

12. A surgical marking device for marking tissue, comprising:
- a body including an at least partially hollow interior having a first end and a second end having an opening;
- a cartridge at least partially retained within the opening and holding an ink that is Food and Drug Administration (FDA) approved for use in internal and/or external marking tissue of a mammal during surgical procedures;
- a tip comprising a porous assembly of fibers or fibrous flow-inducing channels fluidly coupled to the cartridge to permit flow of the ink from the body to the tip by capillary action;
- a plunger movably coupled to the body at the first end and configured to control a gas pressure within the at least partially hollow interior of the body via movement of the plunger relative to the body, wherein an increase in the gas pressure increases a pressure of liquid ink contained within the tip and the pressure control controls a flow of the ink outward of the body via the tip during use and wherein the tip is non-reactive with the ink; and
- a pressure release valve for reducing the pressure within the at least partially hollow interior of the body.

13. The device of claim 12, further comprising:
opposing reaction surfaces respectively disposed on the body and the plunger to facilitate the manual generation and application of a force for purposes of moving the plunger deeper into the body.

14. The device of claim 12, further comprising:
complementary threads respectively disposed in the body and the plunger that facilitate control of the position of the plunger with respect to the body via a screwing motion.

15. The device of claim 12, wherein the tip is detachable from a spent ink cartridge and attachable to a replacement ink cartridge that is insertable into the body.

* * * * *